United States Patent [19]
Bissinger

[11] Patent Number: 6,075,068
[45] Date of Patent: Jun. 13, 2000

[54] DENTAL COMPOSITIONS CURABLE BY ROMP

[75] Inventor: Peter Bissinger, Mering, Germany

[73] Assignee: Espe Dental AG, Germany

[21] Appl. No.: 09/161,947

[22] Filed: Sep. 29, 1998

[30] Foreign Application Priority Data

Sep. 29, 1997 [DE] Germany ............ 197 42 981

[51] Int. Cl.$^7$ ............. C08L 45/00; C08L 65/00; A61K 6/083
[52] U.S. Cl. ............. 523/116; 524/176; 524/395; 524/553; 526/170; 526/172; 522/29; 522/66
[58] Field of Search ............. 523/116; 524/553, 524/176, 395; 522/29, 66; 526/170, 172

[56] References Cited

U.S. PATENT DOCUMENTS

| | | | |
|---|---|---|---|
| 5,439,992 | 8/1995 | Yi et al. | 526/73 |
| 5,539,060 | 7/1996 | Tsunogae et al. | 525/338 |
| 5,854,299 | 12/1998 | Muhlebach et al. | 522/66 |

FOREIGN PATENT DOCUMENTS

| | | |
|---|---|---|
| 2198190 | 8/1997 | Canada . |
| 0792881 | 9/1997 | European Pat. Off. . |
| 19608313 | 8/1997 | Germany . |
| 19616183 | 9/1997 | Germany . |

OTHER PUBLICATIONS

Patent Abstract of Japan C–923 Mar. 31, 1992 vol. 16/No. 126.

*Primary Examiner*—Andrew E. C. Merriam
*Attorney, Agent, or Firm*—Birch, Stewart, Kolasch & Birch, LLP

[57] ABSTRACT

The invention relates to dental compositions, containing
(a) 5 to 70 wt. %, based on (a)+(b)+(d), of polymerizable monomers and/or polymers,
(b) 0 to 95 wt. %, based on (a)+(b)+(d), of fillers,
(c) 1.0 to 15 wt. %, based on (a), of at least one initiator or one initiator system,
(d) 0 to 95 wt. %, based on (a)+(b)+(d), of the usual auxiliaries, including pigments, radiopaque additives and/or thixotropy aids,
characterized in that constituent (a) has a chemical structure such that partial or final curing of the dental composition can be effected by ring-opening metathesis polymerization.

The dental compositions are characterized by a rapid polymerization process, leading to partially or fully cured materials, which display little volume shrinkage, little abrasion tendency and good mechanical properties.

19 Claims, No Drawings

DENTAL COMPOSITIONS CURABLE BY ROMP

The present invention describes polymerizable compositions for dental purposes, which can be cured or partially cured by ring-opening metathesis polymerization (ROMP).

Ethylenically-unsaturated monomers, preferably methacrylate and acrylate monomers, have mainly been used until now in polymerizable dental compositions. 2,2-Bis[4,1-phenyleneoxy (2-hydroxy-3,1-propanediyl)-methacrylate]-propylidene (bis-GMA), described by Bowen [U.S. Pat. No. 3,066,112] is used particularly often.

Mixtures of this methacrylate with triethyleneglycol dimethacrylate (TEGDMA) still serve as the standard recipe for dental plastic direct-filling materials. Curing of these compositions is based on a radical polymerization reaction which is initiated by suitably activated radical-forming initiators. The adverse polymerization shrinkage that occurs during polymerization is problematic. For example, during application as filling material, this can lead to the formation of discoloration at the edge of the tooth cavity or even to the development of marginal gaps with the associated risk of secondary caries.

Furthermore, in the literature there are also references to cationically curable dental compositions [R. Bowen, J Dent Res (1956) 35, 360–379], [AT-A-204 687], but these could not be used successfully because the curing times are too long and the cured materials have poor mechanical properties.

The task of the present invention is to provide polymerizable compositions for operative and prosthetic dentistry, based on a polymerization principle which leads to materials that can be partially or fully cured rapidly, and exhibit little polymerization shrinkage but at the same time very good mechanical properties.

This task is fulfilled by the provision of dental compositions which contain:

(a) 5 to 70 wt. %, preferably 15 to 60 wt. %, based on (a)+(b)+(d), of polymerizable monomers and/or polymers, (b) 0 to 95 wt. %, preferably 40 to 80 wt. %, based on (a)+(b)+(d), of fillers, (c) 0.01 to 15 wt. %, preferably 0.1 to 15 wt. %, especially 2.0 to 10 wt. %, based on (a), of at least one initiator or one initiator system, (d) 0 to 95 wt. %, preferably 0 to 30 wt. %, especially 5 to 30 wt. %, based on (a)+(b)+(d), of the usual adjuncts, including pigments, radiopaque additives and/or thixotropy auxiliaries, characterized in that constituent (a) has a chemical structure such that the dental compositions can be cured partially or fully by ring-opening metathesis polymerization (ROMP).

Ring-opening metathesis polymerization is known from the literature and has also been used industrially for some years [Comprehensive Polymer Sci.; 4, 109–142]. Wide application of this method of polymerization has been hampered so far by the sensitivity of the necessary catalysts to oxygen and moisture [J. Feldman, R. R. Schrock; Prog. Inorg. Chem. (1991), 39, 1]. However, there are now several catalysts for ROMP which are almost or even entirely free from these drawbacks [WO-9623829 A1]. Photochemically activated catalysts have now also become available for light-curing ROMP [P. A. van der Schaaf, A. Hafner, A. M ühlebach; Angew. Chem. (1996), 108, 1974–1977].

Now it has been found, surprisingly, that ROMP in conjunction with these newer catalysts is eminently suitable for the production of a large number of compositions that can be used for dental purposes. This applies for example to polymerizable filling materials, fixing cements, bonding mixtures, inlays, onlays, veneer shells, temporary crown and bridge materials, dental-engineering materials, pattern materials and impression materials.

Compounds with the following general formula can be used as monomers or polymers according to constituent (a):

$$M\text{-}A_n$$

where

M denotes H or a linear, branched, cyclic or polycyclic organic or organometallic residue. Possible organic residues are $C_1$–$C_{30}$) alkyl, $C_6$–$C_{20}$ aryl, $C_7$–$C_{30}$ alkaryl or $C_3$–$C_{30}$ cycloalkyl with 0–10 hetero-atoms from the group N, O, Si, P, S and a number n of points of attachment for A. Organometallic residues contain, along with the organic residues stated above, additionally linear, branched, cyclic or polycyclic frameworks of an inorganic nature.

Preferred residues M may be

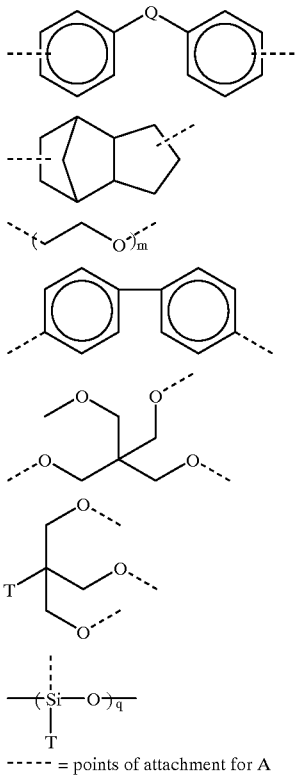

----- = points of attachment for A with the proviso that Q is equal to O, S, $SO_2$ or a linear, branched or cyclic $C_1$–$C_{20}$ alkylene residue, which can also be fluorinated, m is an integer from 1 to 20, T is a linear, branched or cyclic saturated or unsaturated $C_1$–$C_{20}$ hydrocarbon residue and q is an integer from 3 to 20.

A is an unsaturated cyclic or polycyclic organic residue with the general formula

C-D, where C denotes H or a linear, branched or cyclic saturated or unsaturated organic $C_1$–$C_{20}$ residue with 0–10 heteroatoms from the group N, O, Si, P, S and 0–10 carbonyl groups and D is a cyclobutenyl, cyclopentenyl or an unsaturated residue at a designated place in the ring system and optionally additionally at another place in the ring system, with the general formula

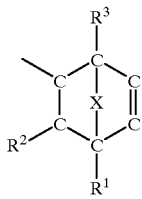

in which:
R$^1$, R$^2$, R$^3$ denote H or a linear, branched or cyclic saturated or unsaturated organic C$_1$–C$_{20}$ residue with 0–10 hetero-atoms of the group N, O, Si, P, S and 0–10 carbonyl groups, and X denotes O, NH, S or a saturated or unsaturated C$_1$–C$_{30}$ hydrocarbon residue.

Especially preferred compounds that can be polymerized by ROMP are:

I) 2,2-Bis-{4,1-phenyleneoxy-3,1-propanediyl-bicyclo [2.2.1]hept-2-enyl-6-carboxy}-propylidene

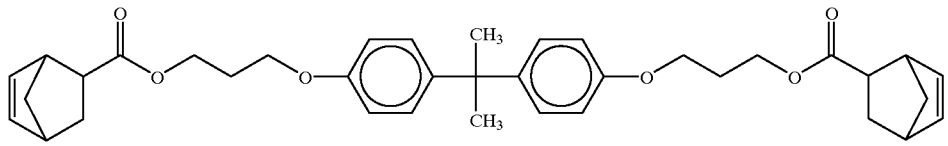

II) 2,2-Bis-{4,1-phenyleneoxy-3,1-propanediyl-7-oxa-bicyclo[2.2.1]hept-2-enyl-6-carboxy}-propylidene

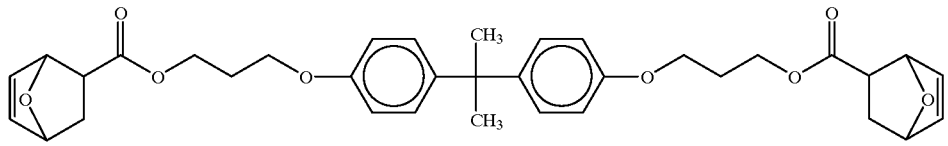

III) Bis-{methanediyl-oxy-3,1-propanediyl-bicyclo[2.2.1] hept-2-enyl-6-carboxyl}tricyclo[5.2.1.0$^{2,6}$]-decane

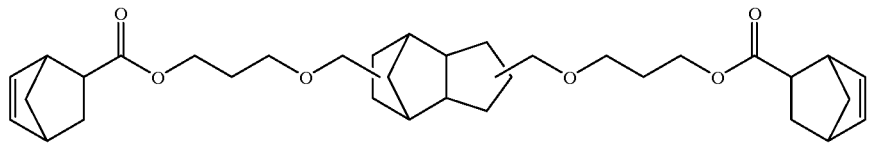

IV) Bis-{methanediyl-oxy-3,1-propanediyl-7-oxa-bicyclo-[2.2.1]hept-2-enyl-6-carboxyl}tricyclo[5.2.1.0$^{2,6}$]-decane

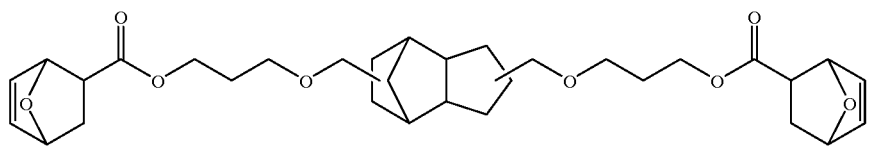

V) 1,1,1-Tris{methanediyl-bicyclo[2.2.1]hept-2-enyl-6-carboxy}propane

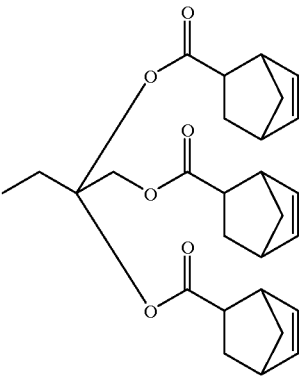

VI) 1,1,1-Tris{methanediyl-7-oxa-bicyclo[2.2.1]hept-2-enyl-6-carboxy}propane

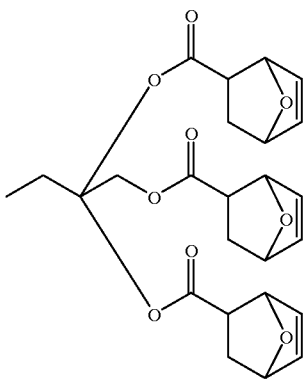

VII) 1,1,1-Tris{methanediyl-oxy-bis(ethanediyloxy)-bicyclo[2.2.1]hept-2-enyl-6-carboxy}propane

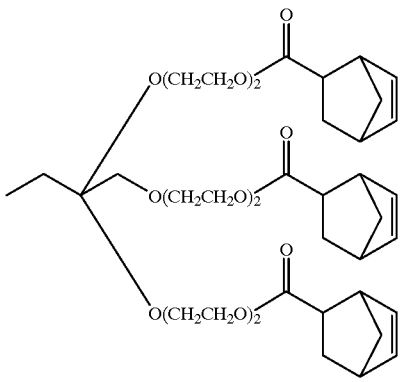

VIII) 1,1,1-Tris{methanediyl-oxy-bis(ethanediyloxy)-7-oxa-bicyclo[2.2.1]hept-2-enyl-6-carboxy}propane

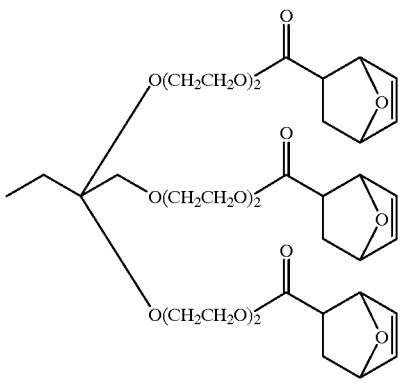

IX) α,ω-Bis{bicyclo[2.2.1]hept-2-enyl-6-carboxy}-polytetrahydrofuran

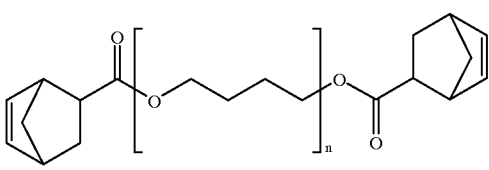

X) α,ω-Bis{7-oxa-bicyclo[2.2.1]hept-2-enyl-6-carboxy}-polytetrahydrofuran

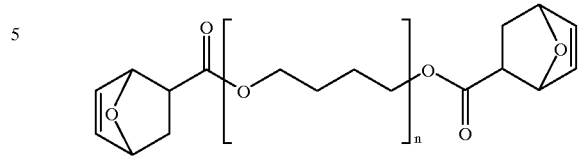

XI) 7-Oxabicyclo[2.2.1]hept-2-ene-5,6-dicarboxylic anhydride

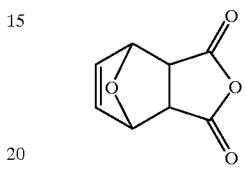

The compounds described here can be used in the disclosed dental compositions either alone or in combination with co-monomers.

These co-monomers can be compounds which are at least simply ethylenically-unsaturated. Ethylenically unsaturated co-monomers whose use is preferred are acrylates or methacrylates. Especially preferred ethylenically unsaturated co-monomers are bis-GMA, TEGDMA, bis-hydroxymethyl)tricyclo-[5.2.1.$^{2,6}$]-decane-diacrylate and 2,2-bis[4,1-phenyleneoxy(3,1-propanediyl)-methacrylate]-propylidene.

Furthermore, at least simply epoxy-functionalized co-monomers can be used. Especially preferred epoxy-functionalized co-monomers are the 3,4-epoxycyclohexylmethyl-3',4'-epoxycyclohexylcarboxylate disclosed in DE-A-196 48 283, and tetrakis-[3,4-epoxycyclohexylethyl]-tetramethyltetracyclosiloxane.

Suitable fillers as constituent (b) are as a rule inorganic fillers. Quartz, ground glasses, silica gels and pyrogenic silicic acids or their granules may be mentioned as examples. It is preferable to use radiopaque fillers as well, at least partially. These may on the one hand be radiopaque glasses, i.e. glasses containing e.g. strontium, barium or lanthanum, or part of the fillers consists of a radiopaque addition, for example yttrium trifluoride, strontium hexafluorozirconate or fluorides of rare-earth metals.

In particular, glasses such as are described in EP-A-0 023 013 are suitable as filler for use in powder-liquid systems. For better incorporation in the polymer matrix it is advantageous to hydrophobize the inorganic fillers. Usual hydrophobizing agents are silanes, for example trimethoxymethacryloyloxypropylsilane or trimethoxyglycidylsilane. The fillers preferably have a mean grain size distribution <20 μm and especially <5 μm, and an upper grain size limit of 150, preferably 70 μm and especially 25 μm. Especially preferred are mixtures of 5–25 wt. % fillers with a mean grain size of 0.02–0.06 μm and 65–85 wt. % fillers with a mean grain size of 1–5 μm.

Various transition metal compounds are known as catalysts of ROMP, and are used according to the particular application of ROMP. For the dental compositions according to the invention, compounds with the following general formula $$WX_nL_{6-n}$$

in combination with

are suitable as constituent (c). In the above formulae: X denotes F, Cl, Br, L denotes a $C_1$–$C_{20}$ alcoholate or $C_6$–$C_{20}$ phenolate with up to 5 hetero-atoms from the group N, O, Si, P, S and substituted up to fivefold with Cl or Br, R denotes a linear or branched $C_1$–$C_{10}$ alkyl residue, n denotes 0–6 and m denotes 0–3, and activation can be effected if necessary with alkyl tin with $C_1$–$C_3$ alkyl residues.

It is also possible to use compounds with the general formula

where:
- M denotes Mo, W, Ta or Nb,
- $L^1$ denotes $OR^3$ or Cl or Br, where $R^3$ is a linear or branched or cyclic $C_1$–$C_{10}$ alkyl residue, which can be fluorinated partially or fully,
- $L^2$ denotes $PR^4_3$ or N=Ar, where $R^4$ is a linear or branched $C_1$–$C_{20}$ alkyl residue or an aromatic $C_7$–$C_{20}$ residue, and Ar is an aromatic $C_7$–$C_{20}$ residue, which may be substituted by linear or branched $C_1$–$C_{10}$ alkyl, an $NH_2$ group or an OH group,
- $R^1$ and $R^2$ denote H or linear or branched or cyclic $C_1$–$C_{15}$ alkyl or $C_6$–15 aryl or $C_7$–$C_{15}$ alkaryl and together $C_1$–$C_{15}$ alkenyl,
- and a and b each denote a value of 0 to 6, with the proviso a+b≠0.

Especially preferred are compounds in which $R^3$ denotes tertiary alkyl residues or in which Ar denotes aromatic residues with alkyl substituents in the 2,6 position.

Furthermore, compounds with the general formula

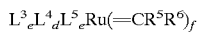

are suitable as constituent (b), where:
- $L^3$ denotes Cl, Br, tosylate or $R^7$, where $R^7$ is a linear or branched or cyclic $C_1$–$C_{10}$ alkyl residue, which may be fluorinated partially or fully,
- $L^4$ denotes $PR^8_3$ or N=Ar, where $R^8$ is a linear or branched $C_1$–$C_{20}$ alkyl residue or an aromatic $C_7$–$C_{20}$ residue and Ar is an aromatic $C_7$–$C_{20}$ residue, which may be substituted by linear or branched $C_1$–$C_{10}$ alkyl, an $NH_2$ group or an OH group,
- $L^5$ denotes benzene or alkyl-substituted $C_7$–$C_{20}$ aromatics,
- $R^5$ and $R^6$ denote H or linear or branched or cyclic $C_1$–$C_{15}$ alkyl or $C_6$–$C_{15}$ aryl or $C_7$–$C_{15}$ alkaryl and together $C_1$–$C_{15}$ alkylene,
- and c, d, e and f each denote a value from 0 to 4, with the proviso: c+d+e+f≠0.

Especially preferred are compounds in which $R^3$ denotes tertiary alkyl residues or in which Ar denotes aromatic residues with alkyl substituents in the 2,6 position.

The last-mentioned catalysts are also suitable for use in water-containing dental compositions, provided the dental composition contains at least 5 wt. % water.

For dental compositions that have this water content, in addition compounds with the following general formula are also suitable as catalysts for ROMP:

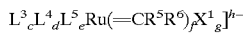

in which:
- $L^3$ denotes Cl, Br, tosylate or R', where R' is a linear or branched or cyclic $C_1$–$C_{10}$ alkyl residue, which may be fluorinated either partially or fully,
- $L^4$ denotes $PR^8_3$ or N=Ar, where $R^8$ is a linear or branched $C_1$–$C_{20}$ alkyl residue or an aromatic $C_7$–$C_{30}$ residue and Ar is an aromatic $C_7$–$C_{20}$ residue, which may be substituted by linear or branched $C_1$–$C_{10}$ alkyl, an $NH_2$ group or an OH group,
- $L^5$ denotes benzene or alkyl-substituted $C_7$–$C_{20}$ aromatics,
- $R^5$ and $R^6$ denote H or linear or branched or cyclic $C_1$–$C_{15}$ alkyl or $C_6$–$C_{15}$ aryl or $C_7$–$C_{15}$ alkaryl and together $C_1$–$C_{15}$ alkylene,
- c, d, e and f denote a value from 0 to 4,
- $X^1$ denotes $L^3$ and
- g and h each denote a value from 0 to 3, with the proviso: c+d+e+f+g+h≠0.

Additionally to the stated catalysts that initiate ROMP, yet other catalysts may be contained as constituent (c), for example radical formers or cation formers. This is the case in particular when the dental compositions according to the invention are only partially cured by ROMP and are finish-cured on the basis of a second reaction mechanism. As radical-forming catalysts it is possible to use substances that can be activated by UV or visible light, for example benzoin alkylethers, benzyl ketals, acylphosphine oxides or aliphatic and aromatic 1,2-diketone compounds, e.g. camphorquinone, and the photochemical polymerization can be accelerated in a known manner by adding activators, such as tertiary amines or organic phosphites.

Suitable initiator systems for initiating radical polymerization by a redox mechanism are for example the systems peroxide/amine or peroxide/barbituric acid derivatives and the like. When using these initiator systems it is advisable to prepare an initiator (e.g. peroxide) and a catalyst component (e.g. amine) separately. The two components are then mixed together homogeneously shortly before use.

As cation formers it is possible to use acid formers, for example Lewis or Broensted acids or compounds that liberate these acids, which initiate cationic polymerization, for example $BF_3$ or its ether adducts ($BF_3*THF$, $BF_3*Et_2O$, etc.), $AlCl_3$, $FeCl_3$, $HPF_6$, $HAsF_6$, $HSbF_6$, $HBF_4$ or substances that initiate polymerization after irradiation by UV or visible light or by heat and/or pressure, for example (eta-6-cumene)(eta-5-cyclopenta-dienyl)iron-hexafluorophosphate, (eta-6-cumene)(eta-5-cyclopenta-dienyl)iron-tetrafluoroborate, (eta-6-cumene)(eta-5-cyclopentadienyl)-iron-hexafluoroantimonate, substituted diaryl-iodonium salts and triaryl-sulphonium salts. As accelerators it is possible to use peroxy compounds such as per-esters, diacyl peroxides, peroxydicarbonates and hydroperoxides. Use of hydroperoxides is preferred. Cumene hydroperoxide in approx. 70–90% solution in cumene can be used as an especially preferred accelerator. The ratio of photoinitiator to cumene hydroperoxide can be varied over a wide range from 1:0.001 to 1:10, though it is preferable to use a ratio from 1:0.1 to 1:6, and the range from 1:0.5 to 1:4 is especially preferred. The use of complexing agents, for example oxalic acid, 8-hydroxyquinoline, ethylenediamine-tetraacetic acid and aromatic polyhydroxy compounds is also possible. Bases, typically tertiary amines, can be added as retarders.

Suitable auxiliaries according to component (d) are for example the stabilizers, pigments or diluents that are usually employed in dentistry.

The dental compositions according to the invention can be made available to the user both as single-component and as multi-component systems. In the case of single-component dental compositions, the catalysts they contain are preferably activated with light, which as a rule leads to rapid final curing of the dental compositions. In this case the dental compositions are preferably in the form of pastes. In the case of multi-component systems the compounds are kept in spatially separate containers and are not mixed together until just before use, by hand or by means of suitable mixing aids. Mixing initiates the curing process and leads to partial or final curing of the whole mass. Either paste-paste systems or powder-liquid systems can be used. If the catalysts are selected so that only partial curing occurs as a result of the mixing process, the compositions preferably contain other initiators that can be activated photochemically, which lead to final curing of the dental compositions by exposing the compositions to light in a second step. In this way it will be possible for the user to work the dental composition in the partly-cured state and then transform it to the fully cured mass for application e.g. in the patient's mouth.

The dental compositions according to the invention are characterized by a rapid polymerization process, leading to partially or fully cured materials which exhibit little volume shrinkage, little abrasion tendency and good mechanical properties.

The following examples explain the invention in more detail.

EXAMPLES

Example 1

Single-component filling material, which is cured by light-induced ROMP 2.0 g of [W(=NPh)(CH2SiMe3)2{OCMe(CF3)2}2] is added to 20 g of compound II, stirring until a clear solution is obtained. This solution is kneaded with 0.5 g of highly-disperse silicon dioxide (Aerosil OX50, from Degussa) and 77.5 g of finely-ground quartz powder, to give a homogeneous paste. For production of test-pieces for the determination of mechanical properties, the paste is placed in appropriate test-piece moulds and cured with light in accordance with ISO Standard 4049.

Example 2

Two-component filling material, which is cured by ROMP 4.0 g of compound VI is kneaded with 0.05 g of highly-disperse silicon dioxide (Aerosil OX50, from Degussa) and 5.95 g of finely-ground quartz powder to a homogeneous paste A2.

0.4 g of ROMP-catalyst based on aryl ruthenate (CGI 452, from Ciba Specialty Chemicals) is kneaded with 0.05 g of highly-disperse silicon dioxide (Aerosil OX50, from Degussa) and 3.0 g of dioctylphthalate and 6.55 g of finely-ground quartz powder to a homogeneous paste B2. For the production of test-pieces for the determination of mechanical properties, 1.0 g each of pastes A2 and B2 are mixed together homogeneously, placed in appropriate test-piece moulds (according to ISO Standard 4049) and removed from the moulds after curing (approx. 5 minutes).

Example 3

Two-component temporary crown and bridge material, which is radical-polymerized in a second curing step 4.6 g of bis-(hydroxymethyl)tricyclo[$5.2.1.0^{2,6}$]-decane-diacrylate is kneaded with 0.4 g of ROMP-catalyst based on aryl-ruthenate (CGI 452, from Ciba Specialty Chemicals), 0.05 g of highly-disperse silicon dioxide (Aerosil OX50, from Degussa) and 4.95 g of finely-ground quartz powder to a homogeneous paste A3.

5.0 g of compound III is kneaded with 0.02 g of camphorquinone, 0.05 g of highly-disperse silicon dioxide (Aerosil OX50, from Degussa) and 4.93 g of finely-ground quartz powder to a homogeneous paste B3.

For preparation of a temporary material, equal quantities of each of pastes A3 and B3 are mixed together homogeneously and placed in the appropriate receiving vessel. After about 2–3 minutes the material reaches an intermediate cure, which does not change further even during quite a long waiting time. The precured material is exposed to visible light for 40 seconds, to achieve final curing.

Example 4

Two-component temporary crown and bridge material, which is polymerized cationically in a second curing step 4.8 g of tetrakis-[3,4-epoxycyclohexylethyl]-tetramethyltetracyclo-siloxane, 0.4 g of ROMP-catalyst based on aryl ruthenate (CGI 452, from Ciba Specialty Chemicals), 0.05 g of highly-disperse silicon dioxide (Aerosil OX50, from Degussa) and 4.75 g of finely-ground quartz powder are kneaded to a homogeneous paste A4.

5.0 g of compound III is kneaded with 0.02 g ferrocenium-hexafluoroantimonate, 0.02 g cumene hydroperoxide, 0.05 g highly-disperse silicon dioxide (Aerosil OX50, from Degussa) and 4.91 g of finely-ground quartz powder to a homogeneous paste B4.

For preparation of a temporary material, equal quantities of each of pastes A4 and B4 are mixed together homogeneously and placed in the appropriate receiving vessel. After about 2–3 minutes the material reaches an intermediate cure, which does not change further even during quite a long waiting time. The precured material is exposed to visible light for 40 seconds, to achieve final curing.

Example 5

Powder-liquid system as dental filling material 1.0 g of compound XI is mixed with 1.0 g of a glass powder (CHELON-FIL Powder, from ESPE, Seefeld). Using a spatula, this powder mix is stirred with 0.6 g of an aqueous solution of $K_2RuCl_5 * xH_2O$ (c=140 mg/ml). For production of test-pieces for determination of mechanical properties, the filling composition is placed immediately after mixing in appropriate test-piece moulds according to ISO Standard 4049 or ISO Standard 9917, until the compositions have set.

TABLE 1

| | Synopsis of mechanical data for the examples according to the invention | | | | |
|---|---|---|---|---|---|
| | Example No. | | | Pertac II (from | Ketac-Fil (from |
| | 1 | 2 | 5 | ESPE, Seefeld) | ESPE, Seefeld) |
| Compressive strength | 392[a] | 405[a] | 155[b] | 420[a] | 165[b] |

TABLE 1-continued

Synopsis of mechanical data for the
examples according to the invention

| | Example No. | | | Pertac II (from ESPE, Seefeld) | Ketac-Fil (from ESPE, Seefeld) |
|---|---|---|---|---|---|
| | 1 | 2 | 5 | | |
| [MPa] | | | | | |
| Bending strength [MPa] | 94[a)] | 92[a)] | 48[b)] | 100[a)] | 35[b)] |
| Volume shrinkage [%][c)] | 1.4 | 1.1 | — | 2.3 | — |
| Abrasion [μm][d)] | 30 | 35 | 87 | 34 | 94 |

[a)]Measurement according to ISO Standard 4049
[b)]Measurement according to ISO Standard 9917
[c)]Measured with ACTA-Linometer (A.J. de Gee, A.J. Feilzer, C.L. Davidson; Dent. Mat. (1993), 9, 11–14)
[d)]Measured with ACTA Abrasion Machine (A.J. de Gee, P. Pallav; J Dent 1994, 22 (1); 21–27)

I claim:
1. Dental composition containing
   (a) 5 to 70 wt. %, based on (a)+(b)+(d), of polymerizable monomers and/or polymers,
   (b) 0 to 95 wt. % based on (a)+(b)+(d), fillers,
   (c) 0.01 to 15 wt. % based on (a), of at least one initiator or initiator system,
   (d) 0 to 95 wt. %, based on (a)+(b)+(d), of an auxiliary,
   wherein constituent (a) has a chemical structure such that partial or final curing of the dental composition can be effected by ring-opening metathesis polymerization, and wherein constituent (c) is selected from one of the following three categories:
a first category of compounds with the general formula

$$WX_nL_{6-n}$$

in combination with $$R_mAlX_{3-m}$$

wherein
   X denotes F, Cl, Br,
   L denotes a $C_1$–$C_{20}$ alcoholate or $C_6$–$C_{20}$ phenolate with up to 5 hetero-atoms from the group N, O, Si, P, S and substituted up to five times with Cl or Br,
   R denotes a linear or branched $C_1$–$C_{10}$ alkyl residue,
   n denotes 0–6, and m denotes 0–3,
   and the dental composition may additionally contain an alkyl tin with $C_1$–$C_5$ alkyl residues as an activator;
a second category of compounds with the general formula $$L^1_aL^2_bM=CR^1R^2$$

wherein
   M denotes Mo, W, Ta or Nb,
   $L^1$ denotes $OR^3$ or Cl or Br, wherein $R^3$ is a linear or branched or cyclic $C_1$–$C_{10}$ alkyl residue, which may be partially or fully fluorinated,
   $L^2$ denotes $PR^4_3$ or N=Ar, wherein $R^4$ is a linear or branched $C_1$–$C_{20}$ alkyl residue or an aromatic $C_7$–$C_{20}$ residue and Ar is an aromatic $C_7$–$C_{20}$ residue, which may be substituted with linear or branched $C_1$–$C_{10}$ alkyl, an $NH_2$ group or an OH group,
   $R^1$ and $R^2$ each denote H or linear or branched or cyclic $C_1$–$C_{15}$ alkyl or $C_6$–$C_{15}$ aryl or $C_7$–$C_{15}$ alkaryl or together $C_7$–$C_{15}$ alkylene, and a and b each denote a value of 0–6, with the proviso: a+b≠0; and a third category of compounds with the general formula $$L^3_cL^4_dL^5_eRu(=CR^5R^6)_f$$

wherein
   $L^3$ notes Cl, Br, tosylate or R, wherein R is a linear or branched or cyclic $C_1$–$C_{10}$ alkyl residue, which may be partially or fully fluorinated,
   $L^4$ denotes $PR^8_3$ or N=Ar, wherein $R^8$ is a linear or branched $C_1$–$C_{20}$ alkyl residue or an aromatic $C_7$–$C_{20}$ residue and Ar is an aromatic $C_7$–$C_{20}$ residue, which may be substituted by linear or branched $C_1$–$C_{10}$ alkyl, an $NH_2$ group or an OH group,
   $L^5$ denotes benzene or alkyl-substituted $C_7$–$C_{20}$ aromatics,
   $R^5$ and $R^6$ each denote H or linear or branched cyclic $C_1$–$C_{15}$ alkyl or $C_6$–$C_{15}$ aryl or $C_7$–$C_{15}$ alkaryl or together $C_1$–$C_{15}$ alkylene, and c, d, e and f each denote a value from 0 to 4, with the proviso: c+d+e+f≠0.

2. Dental composition according to claim 1, wherein said composition contains constituents (a) to (d) in the following proportions:
   (a) 15 to 60 wt. %, based on (a)+(b)+(d)
   (b) 40 to 80 wt. %, based on (a)+(b)+(d)
   (c) 2.0 to 10 wt. %, based on (a), and
   (d) 0 to 30 wt. %, based on (a)+(b)+(d).

3. Dental composition according to claim 1, wherein constituent (a) comprises monomers with the following general formula $$M-A_n$$

wherein
   M denotes H or a linear, branched, cyclic or polycyclic organic or organometallic residue, and the organic residues can be selected from $C_1$–$C_{30}$ alkyl, $C_6$–$C_{20}$ aryl, $C_7$–$C_{30}$ alkaryl and $C_3$–$C_{30}$ cycloalkyl with 0–10 hetero-atoms from the group N, O, Si, P, S and a number of n attachment points for A, and the organometallic residues additionally contain, as well as the organic residues stated above, linear, branched, cyclic or polycyclic structures of an inorganic nature,
   A denotes an unsaturated cyclic or polycyclic organic residue with the general formula $$C-D$$

wherein

C is a linear, branched or cyclic saturated or unsaturated organic $C_1$–$C_{20}$ residue with 0–10 hetero-atoms from the group N, O, Si, P, S and 0–10 carbonyl groups, and D is a cyclobutenyl, cyclopentenyl or an unsaturated residue in a designated position and optionally additionally in another position in the ring system, with the general formula

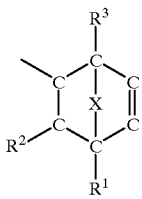

in which:

$R^1$, $R^2$, $R^3$ denote H or a linear, branched or cyclic saturated or unsaturated organic $C_1$–$C_{20}$ residue with 0–10 hetero-atoms from the group N, O, Si, P, S and 0–10 carbonyl groups, and X denotes O, NH, S or a saturated or unsaturated $C_1$–$C_{30}$ hydrocarbon residue.

4. Dental composition according to claim 1, wherein the dental composition additionally contains at least 5 wt. % water based on the total composition.

5. Dental composition according to claim 1, wherein constitutent (c) comprises compounds with the general formula

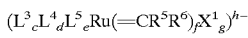

wherein $L^3$ notes Cl, Br, tosylate or R, wherein $R^7$ is a linear or branched or cyclic $C_1$–$C_{10}$ alkyl residue, which may be partially or fully fluorinated, $L^4$ denotes $PR^8{}_3$ or N=Ar, wherein $R^8$ is a linear or branched $C_1$–$C_{20}$ alkyl residue or an aromatic $C_7$–$C_{20}$ residue and Ar is an aromatic $C_7$–$C_{20}$ residue which may be substituted by linear or branched $C_1$–$C_{10}$ alkyl, an $NH_2$ group or an OH group, $L^5$ denotes benzene or alkyl-substituted $C_1$–$C_{20}$ aromatics, $R^5$ and $R^6$ each denote H or linear or branched or cyclic $C_1$–$C_{15}$ alkyl or $C_6$–$C_{15}$ aryl or $C_7$–$C_{15}$ alkaryl or together $C_1$–$C_{15}$ alkylene, c, d, e and f each denote a value from 0 to 4, $X^1$ denotes $L^3$, and g and h each denote a value from 0 to 3, with the proviso that c+d+e+f+g+h≠0 and with the proviso that the dental composition contains 5 wt. % water, based on constituent (c).

6. Dental composition according to claim 1, wherein said composition additionally contains a radical polymerization initiator for final curing in a second step by radical polymerization.

7. Dental composition according to claim 1, wherein said composition additionally contains a cationic polymerization initiator for final curing in a second step by cationic polymerization.

8. A method for the production of a product selected from the group consisting of polymerizable filling materials, fixing cements, bonding mixes, inlays, onlays, veneer shells, temporary crown and bridge materials, dentistry materials, pattern materials and impression materials, which comprises mixing the components (a)–(d) of claim 1 to obtain said product.

9. Dental composition according to claim 3, wherein said composition contains constituents (a) to (d) in the following proportions:

(a) 15 to 60 wt. %, based on (a)+(b)

(b) 40 to 80 wt. % based on (a)+(b)

(c) 2.0 to 10 wt. %, based on (a), and (d) 5 to 30 wt. %, based on (a)+(b).

10. Dental composition according to claim 1, which further comprises a dental surface.

11. Dental composition according to claim 2, which further comprises a dental surface.

12. Dental composition according to claim 3, which further comprises a dental surface.

13. Dental composition according to claim 4, which further comprises a dental surface.

14. Dental composition according to claim 5, which further comprises a dental surface.

15. Dental composition according to claim 1, wherein constituent (c) is the first category of compounds.

16. Dental composition according to claim 1, wherein constituent (c) is the second category of compounds.

17. Dental composition according to claim 8, wherein constituent (c) is the third category of compounds.

18. Dental composition according to claim 1, wherein the auxiliary is selected from the group consisting of pigments, radiopaque additives and thixotropy aids, and mixtures thereof.

19. Dental composition according to claim 18, which further comprises a dental surface.

* * * * *